United States Patent [19]

Grollier et al.

[11] Patent Number: 4,481,185

[45] Date of Patent: Nov. 6, 1984

[54] STABLE EMULSIONS OBTAINED FROM A NATURAL EMULSIFIER STABILIZED WITH ALOES JUICE

[75] Inventors: Jean-Francois Grollier, Paris; Francoise Boudy, Levallois-Perret, both of France

[73] Assignee: Societe Anonyme dite: L'Oreal, Paris, France

[21] Appl. No.: 283,448

[22] Filed: Jul. 15, 1981

[30] Foreign Application Priority Data

Jul. 25, 1980 [FR] France .................. 80 16469

[51] Int. Cl.$^3$ .................. A61K 7/42; A61K 7/44; B01J 13/00

[52] U.S. Cl. .................. 424/59; 252/309; 252/312; 424/60; 424/63; 424/168; 424/358; 424/365

[58] Field of Search .................. 424/59, 60, 168, 63, 424/358, 365; 252/309, 312

[56] References Cited

U.S. PATENT DOCUMENTS 3,004,922 10/1961 Buer .................. 252/312
3,062,721 11/1962 Grate .................. 252/312
3,926,840 12/1975 Wendler et al. .................. 252/356

FOREIGN PATENT DOCUMENTS 2437829 4/1980 France .................. 424/195
2443835 11/1980 France .................. 424/180

OTHER PUBLICATIONS

Spalton, Pharmaceutical Emulsions & Emulsifying Agents, 8/10/50, pp. 28, 29, 33 to 38, 57, 58, 66, 79 to 90, 93 to 96, 104, 105, 112, 119, 121, 126, 128.
Brown, Presented at the Soc. of Cosm. Chemists Annual Scientific Meeting, Poster Session II, Dec. 6, 1979.
Mitsui et al., J. Soc. Cosm. Chemists, 3/1969, vol. 20, pp. 199–213.
Harry, The Principles & Practice of Modern Cosmetics, 12/1974, vol. I, pp. 327–330.
Traven, The Complete Book of Natural Cosmetics, 12/1974, p. 128.
The Merck Index, 11/1979, 9th Edition, pp. 293 and 310.
Seifen-Öle-Fette-Wachse–1979, vol. 105, pp. 499–502, Hoffenberg.
Aloe Vera–Leung, Drug & Cosmetic Industry, 6/1977, pp. 34 to 36.
Meadows, Chem. Abs. 1981, vol. 94, 71207z, Cosmet. Toiletries, 1980, 95(11), pp. 51–52, 54–56.
Henry, Cosm. & Toiletries, 6/1979, vol. 94, pp. 42, 46, 43, 48 and 50.

*Primary Examiner*—Dale R. Ore
*Attorney, Agent, or Firm*—Wegner & Bretschneider

[57] ABSTRACT

An emulsion of the oil-in-water type is disclosed comprising a natural emulsifier and a stabilizer, the emulsifier being a lecithin or a saponoside and the stabilizer being aloes juice. These emulsions are stable and permit the preparation of cosmetic compositions and pharmaceutical excipients.

11 Claims, No Drawings

STABLE EMULSIONS OBTAINED FROM A NATURAL EMULSIFIER STABILIZED WITH ALOES JUICE

The present invention relates to emulsions and especially to cosmetic emulsions of the oil-in-water type obtained with the aid of a stabilised natural emulsifier.

Emulsions represent an important sector of so-called cosmetic products because they in fact constitute the vehicles for numerous formulations such as creams, milks, make-up, foundations and the like.

These emulsions are obtained by using suitable emulsifiers by means of which either emulsions of the oil-in-water type or emulsions of the water-in-oil type can be produced. The majority of these emulsifiers are synthetic or semi-synthetic products. In fact, few natural emulsifiers are capable of giving emulsions which at one and the same time exhibit good storage stability, good unctuousness and good spreading power.

Because of the mediocre emulsifying properties of the majority of natural emulsifiers, it has not been possible to develop "natural" stable emulsions of the oil-in-water type. Thus lecithin, for example, gives emulsions of inferior quality and inferior stability compared to the emulsions obtained with the aid of synthetic emulsifiers.

The same is true of the saponosides which, though they exhibit good surface-active properties, are nevertheless not good emulsifiers capable of giving emulsions having good storage stability.

In order to overcome the disadvantages of these natural emulsifiers, the investigations of cosmetics chemists have been directed towards suitable stabilisers and it has now been found, according to the present invention, entirely surprisingly, that if these natural emulsifiers, such as lecithin or the saponosides, are combined with aloes juice, the emulsions do not break, even after long periods of storage.

The present invention accordingly provides an emulsion of the oil-in-water type, comprising a water phase, an oil phase, a natural emulsifier and a stabiliser, the said emulsifier being lecithin or a saponoside and the said stabiliser being aloes juice.

Storage tests have in fact shown that even under relatively severe conditions, the emulsions according to the invention exhibit a good appearance, that is to say are unctuous, without lumpiness, and pour easily from their container; furthermore, these emulsions have proved to be very stable and to have excellent cosmetic properties.

As mentioned above, the principal emulsifer of the emulsions according to the invention is either lecithin or a saponoside.

The lecithin can be of vegetable or animal origin and can, in particular, be soya lecithin or egg lecithin.

The saponosides used in the emulsions according to the invention are extracts obtained from various vegetable substances.

The saponosides essentially consist, on the one hand, of a sapogenin and, on the other hand, of an ose.

The sapogenins are generally either of a steroid type or of a triterpene type. Amongst the plants which give extracts in which the sapogenins have a steroid structure, there may in particular be mentioned:

(1) those belonging to the Liliaceae family and especially:

(a) the Smilax (salsaparilla) species, for example: *Smilax aspera* L, *Smilax officinalis*, *Smilax regilii*, *Smilax glaberrina*, *Smilax medica*, *Smilax aristolochiaefolia*, *Smilax papyraceae*, *Smilax febrifuga*, *Smilax ornata*, *Smilax saluberina* and *Smilax china*.

(b) the Asparagus species, for example: *Asparagus officinalis* L, *Asparagus persicus* and *Asparagus tenufolius*.

(c) the yuccas, for example: *Yucca filifera*, *Yucca treculeana*, *Yucca glauca*, *Yocca filamentosa*, *Yucca gloriosa* and *Yucca shottii*, and (d) the Ruscus species, for example: *Ruscus aculeatus* L (butcher's broom).

(2) Those belonging to the Discoreaceae family especially the Discorea species, for example: *Discorea tokoro*, *Discorea mexicana*, *Discorea toxicaria* and *Discorea sylvatica*.

(3) Those belonging to the Amaryllidaceae family, especially the Agave species, for example: *Agave sisalana* and *Agave fourcroydes*.

Amongst the plants which give extracts whose sapogenins have a triterpene structure there may in particular be mentioned:

(1) those belonging to the Rosaceae family, for example: *Quillaya saponaria* (soapbark).

(2) those belonging to the Hippocastanaceae family, for example: *Aesculus hippocastanum* L (horse-chestnut).

(3) those belonging to the Zygophyllaceae family, for example: *Guaiacum officinale* L (guaiacum).

(4) those belonging to the Leguminosae family, for example: *Glycyrrhiza glabra* L (liquorice).

(5) those belonging to the Caryophyllaceae family, and especially: Gypsophila species, for example *Gypsophila paniculata*, *Gypsophila struthium* and *Saponaria officinalis* (soapwort).

(6) those belonging to the Araliaceae family, for example: *Hedera helix* L (ivy).

(7) those belonging to the Polygalaceae family, for example: *Polygala senega*.

(8) those belonging to the Sapindaceae family, for example: *Sapindus saponaria*.

The extracts of the various plants enumerated above can be obtained in accordance with various processes and especially by maceration, digestion, decoction, infusion, lixivation or expression.

All these extraction methods are well known to those skilled in the art and are, in particular, described in the book: "L'officine" ("The Apothecary's Workshop") by Dorvault—published by Vigot, 1978, pages 569 to 573.

It is also possible to use, for obtaining plant extracts, the processes described in French Pat. Nos. 2,126,523, 2,227,876 and 2,241,563 and more especially the process described in French Pat. No. 1,520,375.

This latter process consists of treating the plants (roots, barks, leaves, flowers or fruits, for example), which have first been ground, with an aliphatic alcohol having from 1 to 3 carbon atoms (e.g. methyl, ethyl or isopropyl alcohol), of, say, 65-75% strength, and concentrating the alcohol in vacuo until a product having a pasty consistency is obtained. The extract obtained is then taken up in boiling water, the mixture is cooled and the insoluble matter is filtered off. The water-soluble fraction can then be concentrated to give fluid or dry extracts or can, if desired, be treated afresh so as to obtain purer extracts or extracts richer in saponosides. According to the invention, the use of spray-dried products is preferred.

For certain species of plants, the aliphatic alcohol can be replaced by a mixture of water and ethyl acetate or acetone.

The extracts obtained by these processes contain saponosides whose sapogenins have either a steroid structure or a triterpene structure.

In general, the extracts used according to the invention are mixtures which can contain different saponosides, present in an amount of at least 10% by weight, based on solids.

Thus there may be mentioned, by way of example, ivy extract containing 50 to 60% of saponosides, 50% strength salsaparilla extract, 40 to 50% strength soapwort extracts, 50% strength polygala senega extract and 50 to 70% strength horse-chestnut extracts.

According to a variant, the extracts can be enriched in one or more saponosides and are preferably obtained by the process of purification described in French Pat. No. 1,520,375, which process generally gives extracts containing at least 90% by weight of at least one saponoside.

Amongst the saponosides which can be used, there may be mentioned those whose steroid sapogenins are the following: asperoside (*Smilax aspera*), sarsapogenin (*Smilax regilii, Smilax medica* and Yucca species), and smilagenin (*Smilax ornata*).

Amongst the saponosides which can be used, there may also be mentioned those whose triterpine sapogenins are the following: quillaic acid (*Quillaya saponaria* and *Saponaria officinalis*), gypsogenin and gypsogenic acid (Gypsophila and *Saponaria officinalis*), hederagenin (*Hedera helix* and *Sapindus saponaria*), oleanolic acid (*Hedera helix*, Panax, ginseng and guaiacum), senegenin (*Polygala senega*), protoescigenin (*Aesculus hippocastanum*) and glycyrrhetic acid (*Glycyrrhiza glabra*).

According to the invention, the principle emulsifying agent consisting of lecithin or a saponoside is generally present in the emulsion at a concentration of 3 to 30% relative to the total weight of the emulsion.

If, according to the invention, the emulsifier is a saponoside, it is preferably combined with an agent which increases the viscosity, such as a pectin, alginate, carragheenate or vegetable gum.

According to a variant, the stabiliser can be an aqueous extract of aloes juice obtained according to one of the methods described above for the preparation of saponoside extracts.

After spray-drying, the extracts are in the form of a powder which usually contains, amongst other compounds, aloesin, aloesin p-hydroxycinnamate and anthracene compounds such as barbaloin, isobarbaloin and aloe-emodin.

Amongst the various species of aloes of which the juice or one of its aqueous extracts can be used in the emulsions according to the invention there may in particular be mentioned:

*Aloe socotrina* or *Aloe Perryi Baker, Aloe ferox* L and its hybrids, *Aloe africana* Mill, *Aloe spicata* and *Aloe perfoliata* L, and *Aloe vera* L, *Aloe vulgaris* or *Aloe barbadensis*.

These various species are sold under the following names:

Socotrine aloes for *Aloe socotrina*,
Cape aloes for *aloe ferox* and its hybrids,
Curacao aloes or Barbados aloes for *Aloe vera* L and
Indian aloes for *Aloe vulgaris*.

According to the invention, the juice of aloes, or the aqueous extract (expressed as solids) is generally present in the emulsions according to the invention at a concentration of 0.3 to 30% relative to the total weight of the emulsion.

As aloes juice or one of its aqueous extracts is used as a stabiliser this can sometimes make it possible to impart anti-sunburn properties to the compositions.

The active principles of aloes juice in fact have an ultraviolet absorption spectrum which exhibits a peak at about 290 nm–300 nm, that is to say in the erythematous region.

These anti-sunburn properties are known and have more especially been described in the article by G. Proserpio, Cosmetics and Toiletries, Volume 91, March 1976.

Consequently, according to a preferred embodiment of the invention, the emulsions can be used unmodified as anti-sunburn products, without it being necessary to add thereto other compounds exhibiting such properties.

The aloes juice extracts must not be confused with the extracts obtained from mucilages which have no stabilising action whatsoever in the compositions according to the invention and furthermore do not exhibit any anti-sunburn property whatsoever.

A large variety of products can be used to constitute the "oil" phase of the emulsions according to the invention, such products being mineral oils, such as vaseline oil (liquid petrolatum), and modified or unmodified vegetable or animal oils such as sweet almond oil, avocado oil, calophyllum oil, castor oil, olive oil, lanolin and its derivatives, perhydrosqualene and saturated esters, or synthetic oils, such as ethyl palmitate, isopropyl palmitate, alkyl myristates, such as isopropyl myristate, butyl myristate and decyl myristate, hexyl stearate, triglycerides of octanoic and decanoic acid, cetyl ricinoleate, stearyl octanoate (Purcellin oil) and hydrogenated polyisobutene.

The oil phase of the emulsions can also contain certain waxes and especially carnauba wax, beeswax, ozokerite, candelilla wax and microcrystalline waxes, or silicone oils, for example dimethylpolysiloxane.

However, with the object of obtaining so-called natural emulsions, it is preferred to use oils of vegetable origin such as sweet almond oil, groundnut oil, wheatgerm oil, linseed oil, jojoba oil, apricot kernel oil, walnut oil, palm oil, pistachio oil, sesame oil, colza oil, cade oil, corn germ oil, peach kernel oil, poppyseed oil, pine oil, castor oil, soya oil, avacado oil, safflower oil, coconut oil, hazelnut oil, olive oil, grapeseed oil or sunflower oil.

The present invention also provides cosmetic compositions obtained from emulsions such as those defined above, which are in the form of, for example, anti-sunburn creams or milks, creams or milks for care or cleaning of the face, body or hands, or moisturising make-up, foundations or eye make-up.

The pH of these compositions is suitably from 2 to 10 and preferably 3 to 7.

The cosmetic compositions according to the invention can also contain the various ingredients usually employed in cosmetics and in particular dyestuffs, pigments, perfumes and preservatives.

In certain cases it is possible, if desired, to increase the degree of protection against sunburn by introducing certain known anti-sunburn compounds such as derivatives of salicylic acid, derivatives of cinnamic acid, derivatives of para-aminobenzoic acid, derivatives of benzophenone and derivatives of camphor.

The emulsions according to the invention can also be used as pharmaceutical excipients for various active products and be in the form of, for example, creams, ointments or balms.

The following Examples further illustrate the present invention.

EXAMPLE 1

A milk in the form of an oil-in-water emulsion is prepared, according to the invention, by mixing the following ingredients:
- soapwort extract (spray-dried product obtained after extraction of soapwort roots with aqueous alcohol, and containing from 40 to 60% of saponins): 5 g
- colza oil: 33 g
- "Pectine rouge 3 G" (slightly esterified fruit pectin sold by Unipectine): 1 g
- Dry aqueous extract of aloes juice (spray-dried product obtained after aqueous extraction of the juice of *Aloe ferox* L): 5 g
- "Kathon CG" (a mixture of 5-chloro-2-methyl-isothiazol-4-en-3-one, 2-methyl-isothiazol-4-in-3-one and magnesium chloride and calcium chloride, in the form of an aqueous solution containing 1.5% of active materials) sold by Messrs. Rohm and Haas: 0.3 g
- water, q.s.p.: 100 g The pH is about 4.

No settling-out whatsoever of this milk was observed after storage for a lengthy period.

If, in the preceding example, the aloes juice extract is omitted, the milk begins to settle out after 2 to 3 hours. After 24 hours, settling out is very extensive.

To obtain the emulsion, the "Pectine rouge 3 G" is first of all solubilised in water, thereafter the soapwort extract is solubilised, and the preservative is added. Then, the aloes extract is added a little at a time. After complete solubilisation, the emulsion is produced by introducing the oil, a little at a time, with moderate to vigorous stirring.

In this example, the colza oil can be replaced by an equal amount of olive oil.

EXAMPLE 2

A milk in the form of an oil-in-water emulsion is prepared, according to the invention, by mixing the following ingredients:
- ivy extract (spray-dried product obtained after aqueous-alcoholic extraction of ivy leaves, and containing 50 to 60% of saponins): 5 g
- colza oil: 33 g
- Pectine rouge 3 G (as defined in Example 1): 1 g
- Sodium bisulphite (35° Bé): 1 cc
- Dried aqueous extract of aloes juice: 5 g
- Kathon CG (as defined in Example 1): 0.3 g
- water, q.s.p.: 100 g The pH is about 4.

This milk exhibits excellent storage stability, without any settling-out being observed.

The colza oil can be replaced by other oils such as, for example, olive oil.

If, in this emulsion, the aloes juice extract is omitted, the emulsion begins to separate out after a few hours. After 24 hours at ambient temperature, settling-out is very extensive.

EXAMPLE 3

A milk in the form of an oil-in-water emulsion is prepared, according to the invention, by mixing the following ingredients:
- 100% strength soya lecithin: 15 g
- colza oil: 30 g
- sodium bisulphite (35° Bé): 1 cc
- dried aqueous extract of aloes juice: 5 g
- "Kathon CG" (as defined in Example 1): 0.3 g
- water, q.s.p.: 100 g The pH is about 4.

This milk is perfectly homogeneous, exhibits excellent storage stability and provides good protection against sunburn.

In this example, the soya lecithin can be replaced by a corresponding amount of egg lecithin. Equally, the colza oil can be replaced by a corresponding amount of another oil such as, for example, olive oil.

If, in the preceding example, the aloes juice extract is omitted, the milk is not homogeneous. After 24 hours, phase separation, and the presence of oil on the surface, are observed.

EXAMPLE 4

An oil-in-water emulsion is prepared according to the invention by mixing the following ingredients:
- 100% strength soya lecithin: 20 g
- colza oil: 20 g
- Cape aloes juice: 4 g
- Kathon CG (as defined in Example 1): 0.3 g
- water, q.s.p.: 100 g The pH is 5.

This emulsion is in the form of a homogeneous cream. If, in this emulsion, the aloes juice is omitted, large lumps form after a few minutes.

In this example, the soya lecithin can be replaced by other lecithins, for example egg lecithin, and the colza oil can also be replaced by other oils, for example olive oil or sunflower oil.

EXAMPLE 5

An oil-in-water emulsion is prepared according to the invention by mixing the following ingredients:
- 100% strength soya lecithin: 15 g
- sunflower oil: 30 g
- SOCOTRINE aloes juice: 0.3 g
- Kathon CG: 0.3 g
- water, q.s.p.: 100 g The pH is 5.

A thick, homogeneous and stable milk is obtained, which is excellent for treatment of dry facial skin.

EXAMPLE 6

An oil-in-water emulsion is prepared according to the invention by mixing the following ingredients:
- egg lecithin: 16 g
- olive oil: 32 g
- Cape aloes juice: 2 g
- Kathon CG: 0.3 g
- water, q.s.p.: 100 g The pH is 5.

A thick and homogeneous milk is obtained.

EXAMPLE 7

An oil-in-water emulsion is prepared according to the invention by mixing the following ingredients:
- 100% strength soya lecithin: 22 g olive oil: 25 g
Curacao aloes juice: 4.5 g
Kathon CG: 0.3 g
water, q.s.p.: 100 g
The pH is 4.6.

A thick, slightly gelled and homogeneous milk is obtained.

EXAMPLE 8

An emulsion of the oil-in-water type is prepared according to the invention by mixing the following ingredients:
egg lecithin: 25 g
sunflower oil: 15 g
SOCOTRINE aloes juice: 1.5 g
Kathon CG: 0.3 g
water, q.s.p.: 100 g
The pH is 5.

A thick and homogeneous milk is obtained.

EXAMPLE 9

An oil-in-water emulsion is prepared according to the invention by mixing the following ingredients:
egg lecithin: 20 g
colza oil: 31 g
*Aloe ferox* L juice: 15 g
Kathon CG: 0.3 g
water, q.s.p.: 100 g
The pH is 4.6.

A homogeneous gelled cream, which affords good protection against sunburn, is obtained.

If, in the preceding Examples 4 to 9, the aloes juice is omitted, the emulsions are non-homogeneous.

In Examples 4 to 9, colza oil, sunflower oil and olive oil are interchangeable.

The disclosures in the French Patents referred to herein are hereby incorporated by reference.

We claim:

1. In an oil-in-water cosmetic emulsion comprising a water phase, an oil phase, and 3 to 30% a lecithin or saponoside emulsifier, wherein the improvement comprises the addition of 0.3 to 30% aloes juice or an aqueous extract of aloes juice as an emulsion stabilizer.

2. An emulsion according to claim 1 wherein the lecithin emulsifier is soya lecithin or egg lecithin.

3. An emulsion according to claim 1 wherein the saponoside emulsifier is in the form of a plant extract in which the sapogenins are steroidal.

4. An emulsion according to claim 1 wherein the saponoside emulsifier is in the form of a plant extract in which the sapogenins are triterpenoid.

5. An emulsion according to claim 1 wherein the stabilizer comprises aloesin, aloesin p-hydroxycinnamate, barbaloin, isobarboloin and aloe-emodin having an ultraviolet absorption spectrum which exhibits a peak at about 290–300 nm.

6. An emulsion according to claims 1 wherein the "oil" phase comprises at least one vegetable oil selected from the group consisting of is sweet almond oil, groundnut oil, wheatgerm oil, linseed oil, jojoba oil, apricot kernel oil, walnut oil, palm oil, pistachio oil, sesame oil, colza oil, cade oil, corn germ oil, peach kernel oil, poppyseed oil, pine oil, castor oil, soya oil, avocado oil, safflower oil, coconut oil, hazelnut oil, olive oil, grapeseed oil and sunflower oil.

7. An emulsion according to claim 1 having a pH from 2 to 10.

8. An emulsion according to claim 7 having a pH from 3 to 7.

9. An emulsion according to claim 1 in the form of an anti-sunburn cream or milk, a cream or milk for the face, body or hands, a make-up, a foundation or an eye make-up product.

10. An emulsion according to claim 1 containing at least one anti-sunburn agent which is a derivative of salicyclic acid, a derivative of cinnamic acid, a derivative of para-amino-benzoic acid, a derivative of benzophenone or a derivative of camphor.

11. An emulsion according to claim 1 containing one or more cosmetic adjuvants which are dyes, pigments, perfumes or preservatives.

* * * * *